(12) United States Patent
Wang et al.

(10) Patent No.: US 10,022,410 B2
(45) Date of Patent: Jul. 17, 2018

(54) HEMOSTATIC PREPARATION CONTAINING AN EXTRACT OF GOLDEN MOSS

(75) Inventors: Yi-Lan Wang, Belle Mead, NJ (US); Xintian Ming, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 1480 days.

(21) Appl. No.: 12/975,589

(22) Filed: Dec. 22, 2010

(65) Prior Publication Data

US 2012/0164224 A1 Jun. 28, 2012

(51) Int. Cl.

| | |
|---|---|
| A61K 36/12 | (2006.01) |
| A61K 36/00 | (2006.01) |
| A61K 36/287 | (2006.01) |
| A61K 9/00 | (2006.01) |
| A61K 38/39 | (2006.01) |
| A61L 26/00 | (2006.01) |

(52) U.S. Cl.
CPC ............ *A61K 36/12* (2013.01); *A61K 9/0014* (2013.01); *A61K 36/287* (2013.01); *A61K 38/39* (2013.01); *A61L 26/0038* (2013.01); *A61L 26/0057* (2013.01); *A61L 2400/04* (2013.01)

(58) Field of Classification Search
CPC .............................. A61K 36/12; A61K 36/287
USPC ................................................. 424/750, 773
See application file for complete search history.

(56) References Cited

U.S. PATENT DOCUMENTS

| | | | |
|---|---|---|---|
| 4,891,359 A * | 1/1990 | Saferstein et al. ............ | 424/499 |
| 6,045,570 A | 4/2000 | Epstein et al. | |
| 6,652,840 B1 * | 11/2003 | Prevendar ...................... | 424/49 |
| 7,923,431 B2 * | 4/2011 | Wolff ........................... | 514/13.7 |
| 2003/0162708 A1 | 8/2003 | Wolff | |
| 2009/0280184 A1 | 11/2009 | DeSica et al. | |

FOREIGN PATENT DOCUMENTS

| | | |
|---|---|---|
| CN | 1539508 | 10/2004 |
| CN | 101156935 | 4/2008 |
| CN | 101317916 | 12/2008 |
| JP | 2010/227563 | 10/2010 |
| RU | 2226406 | 4/2004 |
| RU | 2369408 | 10/2009 |
| WO | WO 00/18415 | 4/2000 |
| WO | WO 2009/109194 | 9/2009 |
| WO | WO 2010/066869 | 6/2010 |

OTHER PUBLICATIONS

Wu et al. "The constituents of Cibotium barometz and their permeability in the human Caco-2 monolayer cell model", Journal of Ethnopharmacology, 125 (2006), pp. 417-422.*
Hu et al. "Lishizhen Medicine and Materia Medica Research" (2006) vol. 17(2): 275-276.*
Huie, Carmen W. "A review of modern sample-preparation techniques for the extraction and analysis of medicinal plants", Anal Bioanal Chem (200), 373:23-30. (Year: 2002).*
International Search Report re: PCT/US2011/065326 dated Mar. 6, 2012.
Hong, W. 'Drug use of hemostatics and the application development in the area of Enshi, Hubei' Chinese journal of ethnomedicine and ethnopharmacy pp. 76-78.
Hu, Y. et al Lishizhen Medicine and Materia Medica Research (2006) vol. 17(2): 275-276.
Zhang, L. Chinese Traditional Patent Medicine, (2002) 24(10): 807-808.
International Preliminary Report on Patentability re: PCT/US2011/065326 dated Jun. 25, 2013.
TIPO Search Report re: 100147615 dated May 27, 2015.
Written Opinion re: PCT/US2011/065326 dated Mar. 6, 2012.
Chengguo, J. et al 'Experimental study of acesodyne and hemostasis effects of rhizoma cibotii and processed products thereof as well as pilus ciboti rhizomatis' Collect of academic conference papers of 4th Chinese medicine processed product of China Association of Chinese Medicine (2004) pp. 208-211.
Chengguo J. et al 'Study of acesodyne and hemostasis effects of rhizoma cibotii and processed products thereof as well as pilus ciboti rhizomatis' Chinese Patent Medicine vol. 27, Issue 11 (2005) pp. 1279-1281.
Han, G. Herbal medicine 'Pilus Ciboti Rhizomatis hemostasis experimental study' Chinese Surgery Journal vol. 10, Issue 8 (1962) pp. 507-509.
K'yosev, P.A. Comprehensive Reference Guide to Medicinal Herbs. Moscow, Exmo-press, 2001, pp. 846-847.
Minina S.A. et al., Chemistry and technology of phytopreparatinos, M.: GAEOTAR—Media, 2009, pp. 82-94.
Rujun, Z. 'Clinical observations of Pilus Ciboti Rhizomatis dried alum powder for tooth extraction hemostasis etc.' Chinese Journal of Integrated Traditional and Western Medicine Issue 8 (1985) pp. 483-485.
Q. Wu, et al 'The Constituents of Cibotium barometz and their Permeability in the Caco-2 Monolayer Cell Model' Journal of Ethnopharmacology (2009) vol. 125, pp. 417-422.

* cited by examiner

*Primary Examiner* — Christopher R Tate
*Assistant Examiner* — Deborah Davis
(74) *Attorney, Agent, or Firm* — David R. Crichton; Leo B. Kriksunov

(57) ABSTRACT

The present invention relates generally to agents and devices for promoting hemostasis and, more particularly, to an extract of a plant-based "Traditional Chinese Medicinal" product and devices incorporating such agents for the delivery thereof to bleeding wounds.

14 Claims, 2 Drawing Sheets

HEMOSTATIC PREPARATION CONTAINING AN EXTRACT OF GOLDEN MOSS

FIELD OF THE INVENTION

The present invention relates generally to agents and devices for promoting hemostasis and, more particularly, to the use of an extract of a plant-based "Traditional Chinese Medicinal" product and devices incorporating such extracted plant-based agents for the delivery thereof to bleeding wounds.

BACKGROUND

Blood is a liquid tissue that includes red cells, white cells, corpuscles, and platelets dispersed in a liquid phase. The liquid phase is plasma, which includes acids, lipids, dissolved electrolytes, and proteins. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

In an effort to address the above-described problems, materials have been developed for controlling excessive bleeding.

The previously known materials, such as gelatin, collagen, oxidized cellulose, thrombin, fibrinogen, and other materials have been used, but each of these compositions has its limitations. For example, one type of prior art blood clotting materials are blood-derived proteins or enzymes, including fibrinogen and/or thrombin, which are expensive, need specialized storage conditions, and require extensive purification in order to eliminate the potential for transmission of blood-borne infections.

Traditional Chinese Medicine (TCM) based compounds are typically herbal or plant-based preparations which have been used for hundreds of years and are in many cases based on traditional uses, albeit not necessarily supported by modern controlled studies.

Hemostatic traditional Chinese medicines are traditional Chinese medicines used to stop internal or external bleeding. Some of these medicines have separately claimed the actions of "cooling the blood and stopping bleeding by the astringent property, by removing obstructions and by warming channels" and are suggested for bleeding from all parts of the body, such as hemoptysis, haematemesis, epistaxis, hematuria, bloody stools, metrorrhagia and metrostaxis, purpura and traumatic bleeding. Examples of Chinese herbs that have been demonstrated to have hemostatic abilities, such as Daji Radix Cirsii Japonici, Xiaoji Herba Cephalanoploris and Heuihua Flos Sophorae.

Some TCM preparations are made by methods of long-term ambient temperature infusing of alcohol solutions standing over plant-based TCM materials. Such infusions are typically performed at ambient temperature and used as ethanol solutions.

Golden Moss is considered a plant-based Traditional Chinese Medicine (TCM) that has been used for the treatment of rheumatism, lumbago, sciatica and dysuria. *Cibotium barometz* (also called Golden Moss, Fern Lamb of Tartary, or Gou-Ji) has been traditionally used as anti-inflammatory and analgesic [Q. Wu & X.-W. Yang, J. Ethnopharm 2009, 125, 417-422]. The ground yellow hairs of its rhizomes have been used in poultices on wounds to stop bleeding due to its broad contact surface. However, there is no teaching disclosing that an extract of *Cibotium barometz* can be used for both hemostatic and antimicrobial applications.

Published Application No. CN 101317916A discloses a medicine for curing uterine bleeding, which contains the components with the following weight portions: 3 to 7 portions of *Cibotium barometz*, 7 to 12 portions of angelica, 5 to 8 portions of baical skullcap root, 8 to 12 portions of prepared rehmannia rhizome, 4 to 8 portions of longan pulp, 4 to 8 portions of carbonized human hair, 4 to 7 portions of rhizoma corydalis, 6 to 10 portions of notopterygium root and 7 to 12 portions of white paeony root. The preparation method includes decocting the raw materials and then grinding them for filling medicinal bags. However, this preparation is placed in a liquid for oral administration, not as a topical hemostatic treatment.

SUMMARY OF THE INVENTION

The present invention is directed to a hemostatic preparation, preferably for topical use, comprising an extract of the rhizomes of Golden Moss, a gelatin component, and a saline solution. The gelatin component is preferably an absorbable hemostatic powder matrix, and more preferably wherein the gelatin and extract can be substantially homogenously mixed in combination with a saline solution as a liquid phase.

The extract of the rhizomes of Golden Moss is, in one embodiment, a hemostatic product of an ethanol extraction. The hemostatic preparation can contain from about 1% to about 2.5% of the hemostatically effective ethanol extract of Golden Moss.

The extract of rhizomes of Golden Moss is, in another embodiment, a hemostatic product of a water extraction. The hemostatic preparation can contain from about 0.25% to about 2.5% of the hemostatically effective water extract of Golden Moss.

The hemostatic preparation can further contain effective amounts of one or more additives or compounds selected from the group consisting of antimicrobial agents, surfactants, antioxidants, humectants, wetting agents, lubricants, thickeners, diluents, irradiation stabilizers, e.g. radical scavengers, plasticizers, and stabilizers, more particularly including an extrusion enhancing amount of glycerol, and preferably wherein the glycerol is present at an amount from about 1% to about 20% by weight, based on the weight of the liquid phase of the overall hemostatic preparation.

The present invention further relates to a method of providing a hemostatic treatment to a bleeding site, comprising the steps of forming a hemostatic preparation described above, and applying the hemostatic preparation to the bleeding site.

The present invention further relates to a method of making a semi-liquid hemostatic preparation comprising the steps of boiling rhizomes of Golden Moss in a solvent for at least one hour, preferably for at least 48 hours, removing substantially all of the solvent through evaporation under vacuum to form an extract of Golden Moss, and mixing the hemostatic extract product of Golden Moss with a saline solution and a gelatin powder. The solvent can be a low molecular weight alcohol, such as ethanol or an aqueous based solvent. The gelatin powder can be in the form of an absorbable hemostatic powder matrix, and preferably wherein the gelatin and hemostatic extract product are substantially homogenously mixed in combination with a saline solution as a liquid phase. The hemostatic extract product is preferably substantially free of ethanol.

DETAILED DESCRIPTION OF THE INVENTION

Figure 1:
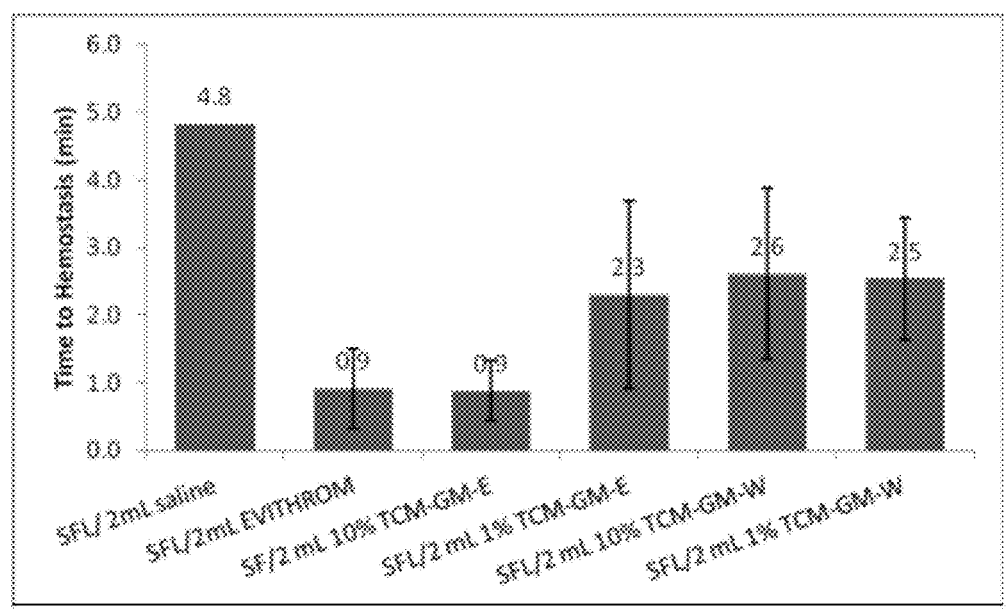
FIG. 1 illustrates the results of in vivo Hemostatic Efficacy Study A, with the times to hemostasis in minutes plotted for several test articles containing hemostatic agents and controls.

The present invention is directed towards a hemostat made of an extract of a plant-based TCM product, preferably an extract of a plant commonly known as Golden Moss, and an absorbable gelatin matrix, having hemostatic and antimicrobial properties.

The inventors discovered that, in one embodiment, an ethanol extract of Golden Moss, a component of Traditional Chinese Medicine (TCM), also known as Traditional Chinese Medicine *Cibotium Barometz*, also called Fern Lamb of Tartary, or Gou-Ji, can be combined with gelatin paste, such as SURGIFLO™, to produce a hemostatic material having high efficacy, comparable to the combination of human thrombin and SURGIFLO™.

Advantageously, the discovered hemostatic agent has antimicrobial properties. Advantageously, the discovered hemostatic agent has an improved stability and is cost effective comparative to conventional blood-derived hemostatic agents.

Preparation of the GM Extract. Dry ground rhizomes of *Cibotium barometz* (Jinzhou, China) can be subjected to an extraction process using either de-ionized (DI) water or, preferably, a 95% ethanol solution that is kept under reflux conditions for at least 48 hours. For purposes of this application, a rhizome is a characteristically horizontal stem of a *Cibotium barometz* plant that is usually found underground, often sending out roots and shoots from its nodes. *Cibotium barometz*, sometimes referred to as golden chicken fern, woolly fern, is a species of tree fern in the fern family Dicksoniaceae. *C. barometz* is native to parts of China and to the western part of the Malay Peninsula.

In one method, a glass flask containing dry ground rhizomes of Golden Moss (D-GM) is placed in a hot water bath that is maintained at a temperature of between 85° C. and 100° C., more preferably about 100° C. Cooling water circulates in the cooling jacket of the reflux tube at a temperature of approximately 4° C. so that the solvent condenses and returns to the glass flask in conventional fashion.

After performing the extraction, the solvent extract material is lyophilized by a standard lyophilization process as known in the art, the lyophilized product is designated GM-W below. The extract can be concentrated at an elevated temperature, such as greater than 50° C., preferably about 60° C. and under reduced pressure to eliminate substantially all solvent, whether ethanol or water, and obtain an extract with 6.8% yield (based on weight of initial dry ground rhizomes), the product designated TCM-GM-E below. The extracts were made into a working solution at 10% and 1% for in vitro and in vivo tests. An ultra-sonicator can be used to make homogenous solutions.

Description of Gelatin Carriers.

The gelatin material of the present invention is preferably a liquid permeable, water insoluble gelatin based sponge or paste. Gelatin, which is a denatured form of the protein collagen, has been used in a variety of wound dressings. Since gelatin gels have a relatively low melting point, they are not very stable at body temperature. Therefore, it is imperative to stabilize these gels by establishing cross-links between the protein chains. In practice, this is usually obtained by treating the gelatin with glutaraldehyde or formaldehyde. Thus cross-linked gelatin may be fabricated into dry sponges which are useful for inducing hemostasis in bleeding wounds or ground into particulate form.

The term "gel" is used herein to denote a swollen, hydrated polymer network which is essentially continuous throughout its volume. A protein gel is composed of an essentially continuous network of linked protein molecules and a liquid (typically aqueous) solvent, which fills the space within the protein matrix. The protein matrix exerts a strong viscous drag on the solvent molecules, preventing them from flowing freely. The component molecules making up the gel network may be linked by ionic, hydrophobic, metallic or covalent bonds. The covalent bond is the most thermally stable of these bonds.

In one embodiment, sterilized compositions of the present invention can contain solid, porous or non-porous particles of a biocompatible polymer suitable for use in hemostasis, a biocompatible liquid and the hemostatic extract as described above as its three primary components. Particles, liquid and hemostatic extract are combined and mixed under conditions effective to provide a substantially homogeneous hemostatic composition comprising a continuous liquid phase comprising the hemostatic extract and having the solid polymer particles homogenously dispersed there through. The amount and average diameter of particles contained in the composition and the relative amounts of the solid, liquid and hemostatic extract is effective to provide the composition with hemostatic and physical properties, as described herein below.

As used herein, "continuous" and "discontinuous" are used in the ordinary meaning of those words in the context of standard nomenclature used to define and describe dispersions.

As used herein, "substantially homogenous" denotes that physical state of the compositions or pastes where the solid particles are uniformly dispersed throughout the continuous liquid phase such that the ratio of solid:liquid and the density of any portion or cross-section of the composition or paste are substantially the same.

As used herein, "sterile" means substantially free of living germs and/or microorganisms and as further recognized and described by governmental standards pertaining to compositions and medical devices described and claimed herein.

As used herein, "hemostatic", or "hemostatic properties", means the ability to stop or minimize bleeding, as one skilled in the art of hemostasis would understand those terms to mean, as further exemplified in the examples of the specification.

A variety of biocompatible natural, semi-synthetic or synthetic polymers may be used to prepare the solid particles used in compositions of the present invention. The polymer selected must be substantially insoluble in the liquid chosen for the particular composition. Preferably, water-insoluble biodegradable polymers that provide mechanical, chemical and/or biological hemostatic activity are used. Polymers that may be used include, without limitation, proteins and polysaccharides. Polysaccharides that may be used include oxidized cellulose, chitosan, chitin, alginate, oxidized alginate and oxidized starch. The biocompatible polymer used to prepare the particles preferably is a cross-linked or denatured protein, such as gelatin, collagen, fibrinogen or fibronectin. A preferred gelatin powder is a partially cross-linked gelatin powder prepared by milling gelatin sponge into particles having an average diameter of from about 40 microns to about 1200 microns, more preferably from about 100 microns to about 1000 microns, as determined by laser diffraction.

Sterile compositions of the present invention preferably comprise a continuous liquid phase in which the hemostatic extract and solid gelatin-based particles are dispersed. Depending upon the particular medical device and use thereof, the liquid may be aqueous or non aqueous. Preferably, the liquid phase is aqueous. Aqueous liquids may include, without limitation, biocompatible aqueous solutions, such as calcium chloride and saline. More preferably, the liquid phase comprises saline. The liquid phase and solid particulate phase are present in relative amounts effective to provide a composition, for example a paste, or slurry, suitable for use in providing hemostasis. In certain embodiments, the weight ratio of solid particles to liquid generally is from about 1:1 to about 1:12, or from about 1:3 to about 1:8 or even about 1:5.

Compositions of the present invention include compositions described herein that are sterile, in that they have been irradiated with a level of, e.g. ionizing irradiation. Such irradiation may include e-beam or gamma irradiation. The level of irradiation and conditions of sterilization, including the time that the compositions are irradiated, are those that provide sterile compositions, as defined herein. Once having the benefit of this disclosure, one skilled in the art will be able to readily determine the level of irradiation necessary to provide sterile compositions.

The hemostatic compositions may further comprise effective amounts of one or more additives or compounds including, but not limited to, antimicrobial agents, surfactants, antioxidants, humectants, wetting agents, lubricants, thickeners, diluents, irradiation stabilizers, e.g. radical scavengers, plasticizers, and stabilizers. For example, glycerol may be added to enhance the extrudability or injectability of the composition. When utilized, glycerol may be present in the compositions at from about 0% to about 20% by weight, based on the weight of the liquid phase. Preferably, the composition may comprise from about 1% to about 10% by weight of glycerol, based on the weight of the liquid phase. More preferably, the compositions may comprise from about 1% to about 5% by weight of glycerol, based on the weight of the liquid phase.

In addition, quaternary amines may be used to provide enhanced properties to the compositions. For example, benzalkonium chloride, Polybrene or Onamer M may be used at levels up to about 1 percent by weight, based on the weight of the liquid phase. Preferably, benzalkonium chloride is used at levels of from about 0.001% to about 0.01% by weight, based on the weight of the liquid phase. More preferably, the compositions may comprise from about 0.002% to about 0.006% by weight benzalkonium chloride, based on the weight of the liquid phase. It is believed that the quaternary amines may serve multiple functions, acting as an antimicrobial agent, a foaming agent, a radical scavenger and as a heparin neutralizer.

Such hemostatic compositions may further comprise heparin neutralizers, additional procoagulants or hemostatic agents, such as fibrinogen, fibrin, Factor Xa, or Factor Vila. By "effective amount", it is meant that amount necessary to provide to the compositions those properties for which the additive is being added. The effective amount also is limited by the maximum amount that may be added without causing detrimental biological effects.

Methods for Incorporating Extract onto Gelatin Carriers.

In one embodiment for making compositions of the invention, a substantially homogenous paste is prepared by mixing the particles with the liquid to form a uniform paste. The liquid includes the hemostatic extract material and may include effective amounts of other additives dissolved therein as described above. Mixing may be accomplished by extrusion or by mixing in a confined space under conditions effective to provide a uniform dispersion of the solid particles in the liquid phase.

Alternately, a mixer, e.g. a double planetary mixer, may be utilized in making compositions of the present invention. The liquid containing the hemostatic extract material is added to the mixer. The liquid may include effective amounts of additives dissolved therein prior to addition of particles to the solution. For example, a saline solution containing hemostatic extract material, glycerol and benzalkonium chloride may be prepared and then added to the mixer. The solid particles are added to the mixer over time with continuous mixing until all ingredients have been added. The mixing is continued until such time as a substantially homogenous composition is formed containing the solid particles uniformly dispersed throughout the continuous liquid phase.

In an alternative embodiment, the hemostatic extract is applied by spraying or printing upon a major surface of substantially dry sponge.

The hemostatic compositions prepared as above can be sterilized to provide sterile compositions comprising the hemostatic extract. In some embodiments the compositions are transferred into a medical device as described above and the device containing the hemostatic composition is sterilized, preferably by ionizing radiation. More preferably, sterilization is by gamma irradiation as exemplified herein.

Medical devices in which the hemostatic compositions of the present invention may be utilized include any device currently being used to apply a flowable or injectable hemostatic paste or slurry to a site, or wound, requiring hemostasis. A sponge can be applied by hand or other means in conventional fashion. The site requiring hemostasis may be the result of an injury or a surgical procedure. Examples of devices or applicators include syringes such as Becton Dickinson or Monoject luer syringes. Other devices are disclosed in detail in U.S. Pat. No. 6,045,570, the contents of which are incorporated by reference in their entirety.

While the following examples demonstrate certain embodiments of the invention, they are not to be interpreted as limiting the scope of the invention, but rather as contributing to a complete description of the invention.

EXAMPLE 1

In vitro Blood Coagulation Study. The inventors performed an in vitro blood coagulation test with 200 µL of each test solution was added to clean glass vials containing 200 µL of fresh porcine blood. The test articles included:

Normal Saline
10% TCM-GM-E Ethanol Extract
10% TCM-GM-W Water Extract
1% TCM-GM-E Ethanol Extract
1% TCM-GM-W Water Extract.

After the vials were sitting at room temperature for 4 minutes, the vials were turned upside down. A significant blood clot was observed in vial containing 10% TCM Ethanol Extract, compared to other test articles. Thus 10% TCM-GM-E Ethanol Extract showed Good Efficacy in the in vitro qualitative testing.

EXAMPLE 2

In Vivo Hemostatic Efficacy Study A. The hemostatic activity study was performed using the porcine spleen biopsy punch model, with the punched wound opening 6 mm wide×3 mm deep made on the spleen and the test article applied to a freshly created wound site followed by an occlusive digital pressure (tamponade). Pressure was initially applied for 30 second and was timed using an electronic timer. Following the 30 sec tamponade, digital pressure was discontinued; the gauze pad on the article was immediately removed. A 30-second hemostasis evaluation period was performed. If free flow bleeding was not observed within 30 seconds, the time to hemostasis was noted, in a minutes seconds format, and testing was concluded for that article. If free flow bleeding was observed, pressure and gauze were reapplied for additional 30 second tamponade and observation periods until hemostasis was achieved or until the testing period reached ten minutes. Hemostasis was determined by the cessation of free flow bleeding in less than ten minutes.

Referring now to FIG. 1, the times to hemostasis in minutes are plotted for several test articles containing hemostatic agents and controls. Test articles included mixtures of gelatin based paste SURGIFLO® (SFL) 6 mL with
2 ml of normal saline
2 mL of 1-10% of extracts (Ethanol, Water) of TCM-GM in normal saline solution
2 ml EVITHROM™ solution containing primarily human thrombin (full composition of Evithrom® contains human thrombin (800-1200 IU/mL), Calcium chloride, human albumin, mannitol, sodium acetate, and water for injection).
In the test, SURGIFLO® was thoroughly mixed with the hemostatic material by the following steps: 1. Drew 2 mL of hemostatic material solution into an empty syringe; 2. Mixed the 2 components by attaching a luer connector to a pre-filled syringe and attaching the hemostatic material solution-containing syringe to the other end of the luer adapter, and then injecting the hemostatic material solution into a pre-filled matrix; 3. Continued to mix the components by pushing the combined material back and forth until the consistency is even), and applied to the wound, with measurements performed as indicated above.

As can be seen in FIG. 1, SFL/10% TCM-GM-E Ethanol Extract showed similar efficacy as SFL/EVITHROM in an in vivo test, with time to hemostasis just under 1 minute.

The results with normal saline used as control showed time to hemostasis as long as 4.8 min. SFL/1% TCM-GM-E as well as SFL/1% TCM-GM-W and SFL/10% TCM-GM-W showed times to hemostasis of the order of 2.3-2.6 minutes.

EXAMPLE 3

In Vivo Hemostatic Efficacy Study B. The hemostatic activity study was performed using a porcine spleen biopsy punch model with the testing parameters similar to these described in the Example 4, with the punched wound opening 6 mm wide×3 mm deep and tamponade time: 30 sec; observation time: 30 sec.

Figure 2:
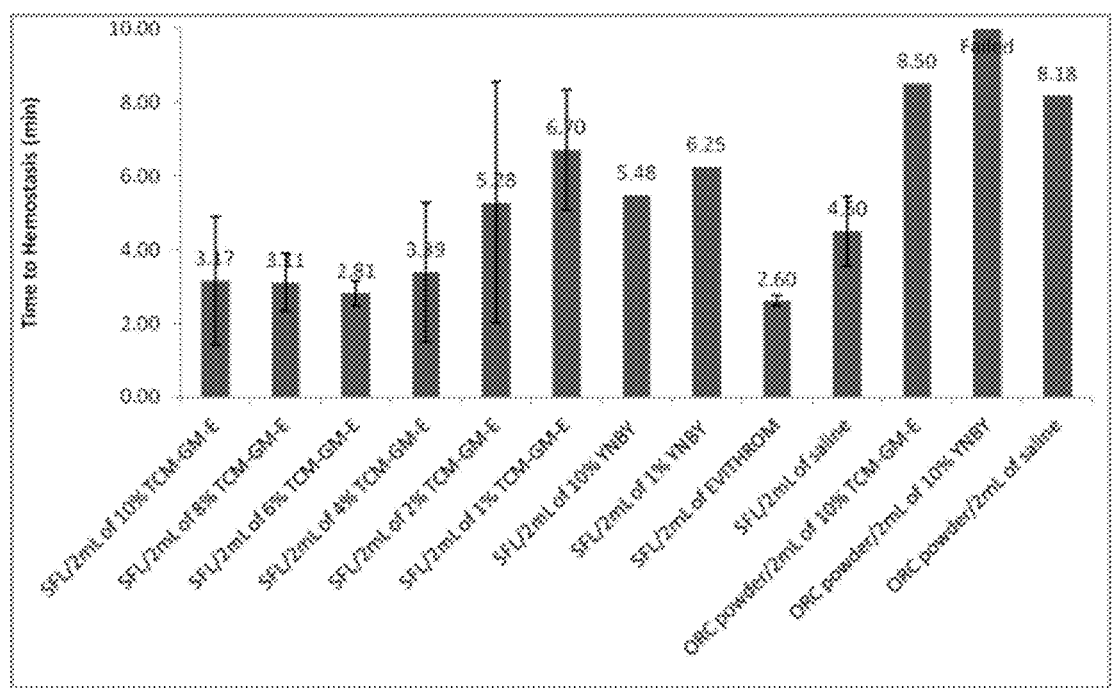
FIG. 2 illustrates the results of in vivo Hemostatic Efficacy Study B, with the times to hemostasis in minutes plotted for several test articles containing hemostatic agents and controls.

Referring now to FIG. 2, the times to hemostasis in minutes are plotted for several test articles containing hemostatic agents and controls. The test articles included
Mixtures of gelatin based paste SURGIFLO® (SFL) 6 mL with
2 ml of normal saline
2 ml of 1-10% of extracts (Ethanol, Water) of TCM-GM in normal saline
2 ml EVITHROM™ solution containing primarily human thrombin (full composition of Evithrom® contains human thrombin (800-1200 IU/mL), Calcium chloride, human albumin, mannitol, sodium acetate, and water for injection).
2 ml of 1-10% YNBY (Yunnan Baiyao Powder), well known TCM preparation specially designated by TCM manuals for use as a hemostat
Test articles also included mixtures based on oxidized regenerated cellulose (ORC) powder, a known and widely used hemostat, said powder made by ball-milling of ORC fabric.
The ORC-based test articles were prepared by mixing
0.983 grams of ORC powder with
2 ml of normal saline
2 ml of 10% of extract (Ethanol) of TCM-GM in normal saline
2 ml of 10% YNBY
In the test, SURGIFLO® or ORC powder were thoroughly mixed with the hemostatic material and applied to the wound, with measurements performed as indicated above.

As can be seen from the data presented in FIG. 2, ORC based compositions showed longer time to hemostasis, ranging from 8-10 minutes. The results of SFL with normal saline used as control showed time to hemostasis as long as 4.5 min.

SFL/4%-10% TCM-GM-E showed times to hemostasis of the order of 2.8-3.4 minutes, with the times for SFL/6%-10% TCM-GM-E particularly fast at 2.8-3.1 minutes, generally comparable to the data obtained with human thrombin-containing EVITHROM which showed hemostsis times of 2.6 minutes.

The test articles containing YNBY and low concentrations of 1%-2% TCM-GM-E showed long times to hemostasis, ranging from 5.2 to 6.7 minutes.

Based on the results presented in Examples 4 and 5, mixtures of gelatin based paste SURGIFLO® with 2 ml 6%-10% TCM-GM-E in saline demonstrated time to hemostasis generally comparable to SURGIFLO® mixtures with human thrombin solutions and significantly better than mixtures with saline.

Based on the results presented in Example 4, mixtures of gelatin based paste SURGIFLO® with 2 ml of 1%-10% TCM-GM-W in saline or with 2 ml 1% TCM-GM-E in saline demonstrated time to hemostasis generally better than SURGIFLO® mixtures with saline.

EXAMPLE 4

Referring now to Table 1, In vitro Antibacterial Efficacy was tested with bacteria challenged in TCM-GM-E containing TSB (tryptic soy broth) medium at about 6 log CFU/ml inoculum. The efficacy was evaluated by enumerating viable bacteria after 24 hr incubation at 37° C. *Control is blank solution of 450 ppm Ethanol in TSB media. The inventors have unexpectedly discovered 3-5 log kill at 450 ppm level for *S. aureus* and *E. coli* indicating efficacy reached at about 450 ppm for both G+ and G− bacteria.

TABLE 1

| In vitro Antibacterial Efficacy | | |
|---|---|---|
| TCM-GM-E (ppm) | *S. aureus* (CFU/mL) | *E. coli* (CFU/mL) |
| Control* | 1 × 10e5 | 2 × 10e5 |
| 225 ppm | 5 × 10e4 | 1 × 10e5 |
| 450 ppm | <10 | 35 |

We claim:

1. A topical hemostatic preparation comprising effective amounts of:
   a solvent extract of the rhizomes of Golden Moss,
   a gelatin in powder form,
   and a saline solution.

2. The hemostatic preparation of claim 1, wherein the gelatin comprises an absorbable hemostatic powder matrix.

3. The hemostatic preparation of claim 2, wherein the gelatin and extract are substantially homogenously mixed in combination with a saline solution as a liquid phase.

4. The hemostatic preparation of claim 3, wherein the extract of the rhizomes of Golden Moss is an ethanol extract.

5. The hemostatic preparation of claim 4, comprising from about 1% to about 2.5% of the ethanol extract of Golden Moss.

6. The hemostatic preparation of claim 3, wherein the extract of Golden Moss is a water extract.

7. The hemostatic preparation of claim 6, comprising from about 0.25% to about 2.5% of the water extract of Golden Moss.

8. The hemostatic preparation of claim 1 further comprising effective amounts of one or more additives or compounds selected from the group consisting of antimicrobial agents, surfactants, antioxidants, humectants, wetting agents, lubricants, thickeners, diluents, irradiation stabilizers, radical scavengers, plasticizers, and stabilizers.

9. The hemostatic preparation of claim 1 further comprising an extrusion enhancing amount of glycerol.

10. The hemostatic preparation of claim 9 wherein the glycerol is present at an amount from about 1% to about 20% by weight, based on the weight of the liquid phase.

11. The hemostatic preparation of claim 1, wherein the solvent extract is a lyophilized concentrate.

12. The hemostatic preparation of claim 1, wherein the solvent extract is a dried concentrate substantially free of solvent.

13. The hemostatic preparation of claim 12, wherein the gelatin has a concentration of between 4 to 10%.

14. The hemostatic preparation of claim 13, wherein the gelatin has a centration of at least 6%.

* * * * *